United States Patent

Hsia et al.

[19]

[11] Patent Number: 6,129,743
[45] Date of Patent: Oct. 10, 2000

[54] OPTIMIZED VENTRICULAR DEFIBRILLATION APPARATUS AND METHOD

[75] Inventors: Peng-Wie Hsia, Richmond, Va.; Rose Province, San Jose; Eric Fain, Menlo Park, both of Calif.

[73] Assignee: Virginia Commonwealth University, Richmond, Va.

[21] Appl. No.: 09/274,300

[22] Filed: Mar. 23, 1999

Related U.S. Application Data

[60] Provisional application No. 60/079,246, Mar. 25, 1998.

[51] Int. Cl.⁷ ................................................. A61N 1/39
[52] U.S. Cl. .................................................... 607/5
[58] Field of Search ....................................... 607/5, 4, 14

[56] References Cited

U.S. PATENT DOCUMENTS 4,996,984  3/1991  Sweeney ....................................... 607/5

*Primary Examiner*—George R. Evanisko
*Attorney, Agent, or Firm*—Whitham, Curtis & Whitham

[57] ABSTRACT

An apparatus and method for defibrillation utilizes a ratio of short and long window moving averages to provide optimum selection of the time for shock delivery.

5 Claims, 7 Drawing Sheets

OPTIMIZED VENTRICULAR DEFIBRILLATION APPARATUS AND METHOD

CROSS-REFERENCE TO RELATED PATENT APPLICATIONS

This application claims the benefit of U.S. Provisional Application No. 60/079,246 filed Mar. 25, 1998.

DESCRIPTION

BACKGROUND OF THE INVENTION

1. Field of the Invention

The invention relates generally to patient cardiac defibrillation and, more particularly, to an apparatus and method for accurately detecting a susceptible period during which time it is easier for an electrical shock to terminate ventricular fibrillation so that the heart can start again on a regular heart rhythm.

2. Description of the Prior Art

Ventricular fibrillation, which is clinically characterized as a period of irregular heart rhythm, is a life threatening condition. Current practice is to provide the patient with an electrical shock to the heart which is intended to correct the heart beat. This is accomplished with devices which are called "defibrillators" and these devices can be either external or internal to the patient's body. Implantable defibrillators may be prescribed to patients which have a chronic propensity for ventricular fibrillation events. In practice, after ventricular fibrillation is detected, the defibrillator delivers the shock. Recently, it has been shown that there are periods of time when a patient's heart is more susceptible to defibrillation (see, Hsia et al., "Genesis of Sigmoidal Dose-Response Curve Defibrillation by Random Shock: A Theoretical Model Based on Experimental Evidence for a Vulnerable Window during Ventricular Fibrillation", *PACE* 13:1326–1342 (1990)). Thus, it would be advantageous to provide a defibrillator which delivers defibrillation energy synchronously with the fibrillation waveforms. U.S. Pat. No. 5,500,008 to Fain seeks to expand on the concepts first proposed by Hsia, and describes an implantable defibrillator which uses synchronized defibrillation.

It would be advantageous clinically if the shock strength required for defibrillation could be reduced. Defibrillation research has utilized the concept of a defibrillation threshold (DFT) to characterize the efficacy of defibrillation. The DFT of an individual heart is defined as the smallest electrical strength which is able to terminate ongoing ventricular fibrillation (VF). This concept has been the standard measurement in defibrillation studies. However, the problem of both high-energy failure and low-energy success during defibrillation has been observed, and can occur randomly due to the probabilistic nature of defibrillation. The fluctuation of the number of excitable cells during VF has been thought to contribute to the uncertainty of defibrillation success when shocks are given randomnly. In the Hsia article referenced above, and in related articles, it was found that a high VF waveform voltage was associated with a greater defibrillation success. This led to the hypothesis that a vulnerable period to defibrillation exists at high VF waveform voltages. In line with this hypothesis, U.S. Pat. No. 5,500,008 to Fain, which is herein incorporated by reference, uses a running average of the absolute values of the peaks and troughs on the fibrillation voltages. However, it would be desirable to improve this method.

SUMMARY OF THE INVENTION

It is an object of this invention to provide an improved VF waveform analysis method and apparatus which provides optimized synchronization of defibrillation shock delivery to cardiac depolarization, and which is less subject to mis-synchronization due to individual variation in VF waveform morphology.

It is yet another object of this invention to provide a system which uses external patches attached to the patient's chest for external defibrillation during rescue operations inside and outside the hospital.

It is still another object of this invention to use VF waveform analysis to improve external defibrillation efficacy.

According to the invention, the new VF waveform analysis method differs in several ways from the prior art. In particular, the method uses at least two moving averages of absolute VF voltages (AVFV) instead of a single running average as described in U.S. Pat. No. 5,500,008. In addition, the method uses new parameters that are derived based on a linear or non-linear combination of the two moving averages instead of the moving average values alone as suggested in U.S. Pat. No. 5,500,008. A long window average provides a measure of coarseness of the VF waveform, while the immediate AVFV is high. The combination of these two parameters will force a shock to be delivered at an early high peak during an envelope of coarse fibrillation. Furthermore, the method uses an adaptive threshold method applied to the waveform parameters to better identify the vulnerable period for defibrillation shock delivery in real time, and for individual patients. Results from a prospective study with this defibrillation technique demonstrated an increase in success rate in trasvenous internal defibrillation in which defibrillation shocks were delivered using an endocardial catheter electrode and skin patch electrodes.

An added benefit of this new apparatus and method is that it can be implemented with the use of an integrated single lead system for transvenous implantation. Sensing between the transvenous lead and the electrically active plus generator "can" is used to sense electrical activity during VF and to deliver a shock therapy at an optimal shock timing.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1A:
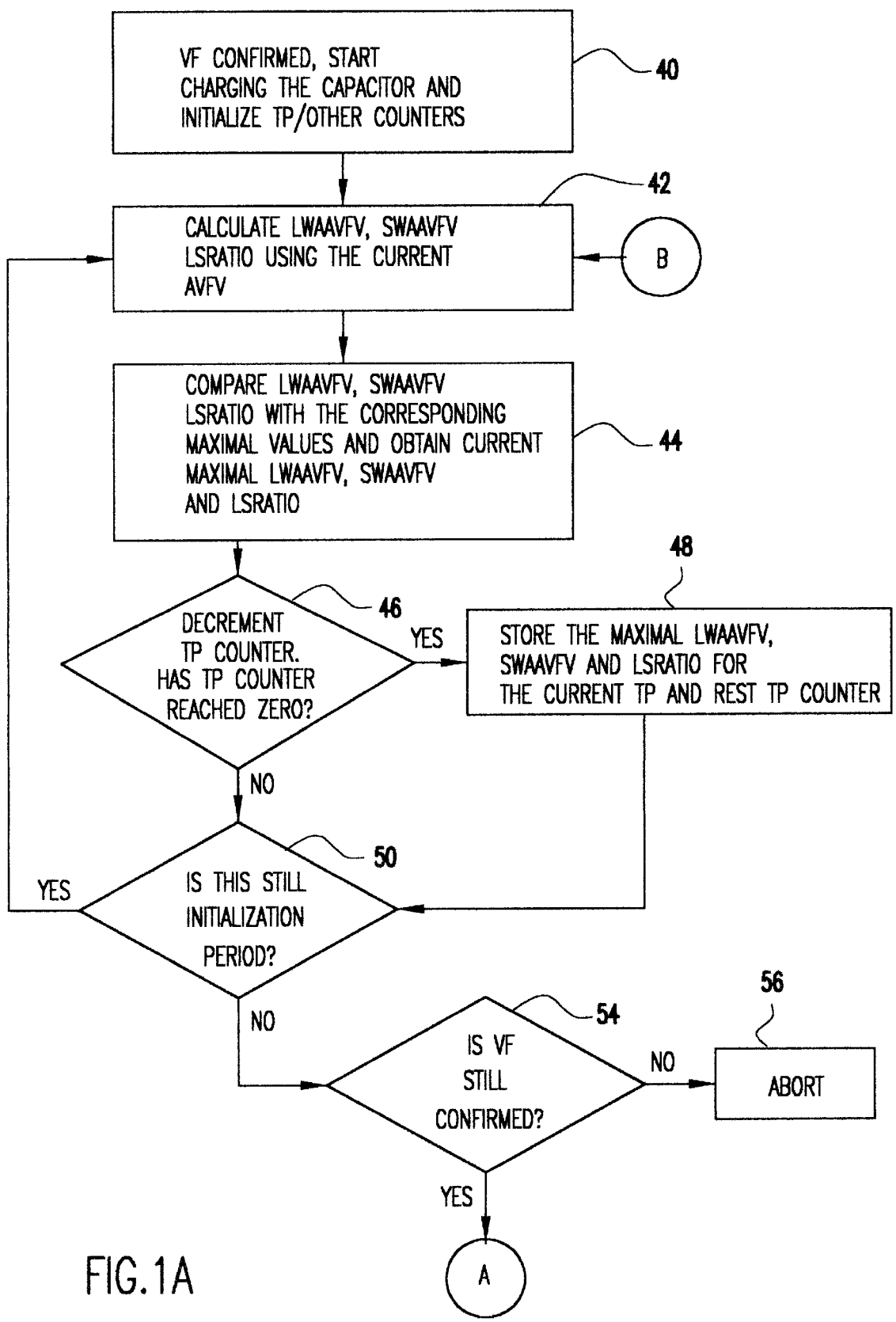
FIGS. 1A–B are flow diagrams illustrating the preferred processing of electrograms in order to deliver defibrillation energy when the heart is most susceptable to being defibrillated.

The present invention is directed toward the provision of an internal or external defibrillator that delivers a defibrillation shock to the heart during a period of ventricular fibrillation (VF) in which the shock is likely to be more successful in defibrillating the heart. Variation in the state of excitability of the cells in the heart results in a cyclic period of increased susceptibility to defibrillation. The susceptible period occurs when the number of excitable cells is low, i.e. a higher state of total depolarization. The absolute VF voltage is a crude marker of the number of excitable cells.

Definitions

In order to give a more precise description of the invention with optimized detection of the vulnerable period to defibrillation, the following abbreviations are defined based on the sampled VF waveform voltage values. Since this invention is to work in a real time process environment, a decision of shock delivery is made at every current data sample (current time) before the next data sample arrives. Therefore all the parameters described herein are based on the current and past VF data samples.

AVFV: Absolute Ventricular Fibrillation Voltage, i.e. the current amplitude value of rectified VF signal at the time of interest.

LWAAVFV: Long Window Average of AVFV, i.e. the running average of AVFV values over a long time window larger than 128 ms (preferred value=128–512 ms).

SWAAVFV: Short Window Average of AVFV, i.e. the running average of AVFV values over a short time window smaller than 64 ms (preferred value=4–64 ms).

LSRATIO: Long Short Ratio, i.e. the ratio of SWAAVFV value over the corresponding LWAAVFV value.

TP: Timeout Period, i.e. a selected period of time during which thresholds for AVFV, LWAAVFV, SWAAVFV and LSRATIO are calculated and still valid for the next TP. The TP is ranged between 1–7 sec (preferred value=3 sec)

IP: Initialization Period, a selected period of time during which thresholds for AVFV, LWAAVFV, SWAAVFV and LSRATIO are determined using a percent of maximum value during that period. The IP is ranged between 3–6 sec. (preferred value=3 sec)

THRESHOLD AVFV: Threshold of AVFV, i.e. an automatically calculated and updated value based on a weighted maximal AVFV value during a TP. If the current AVFV value is greater than this THRESHOLD AVFV, the condition is partially satisfied and a shock can be delivered if other conditions are also met.

THRESHOLD LWA: Threshold of LWA AVFV, i.e. an automatically calculated and updated value based on a weighted maximal LWAAVFV value during a TP. If the current LWAAVFV value is greater than this THRESHOLD LWA, the condition is partially satisfied and a shock can be delivered if other conditions are also met.

THRESHOLD SWA: Threshold of SWAAVFV, i.e. an automatically calculated and updated value based on a weighted maximal SWAAVFV value during TP. If the current SWAAVFV value is greater than this THRESHOLD SWA, the condition is partially satisfied and a shock can be delivered if other conditions are also met.

THRESHOLD LSR: Threshold of LSRATIO, i.e. an automatically calculated and updated value based on a weighted maximal LSRATIO value during TP. If the current LSRATIO value is greater than this threshold LSR, the condition is partially satisfied and a shock can be delivered if other conditions are also met.

Figure 1B:
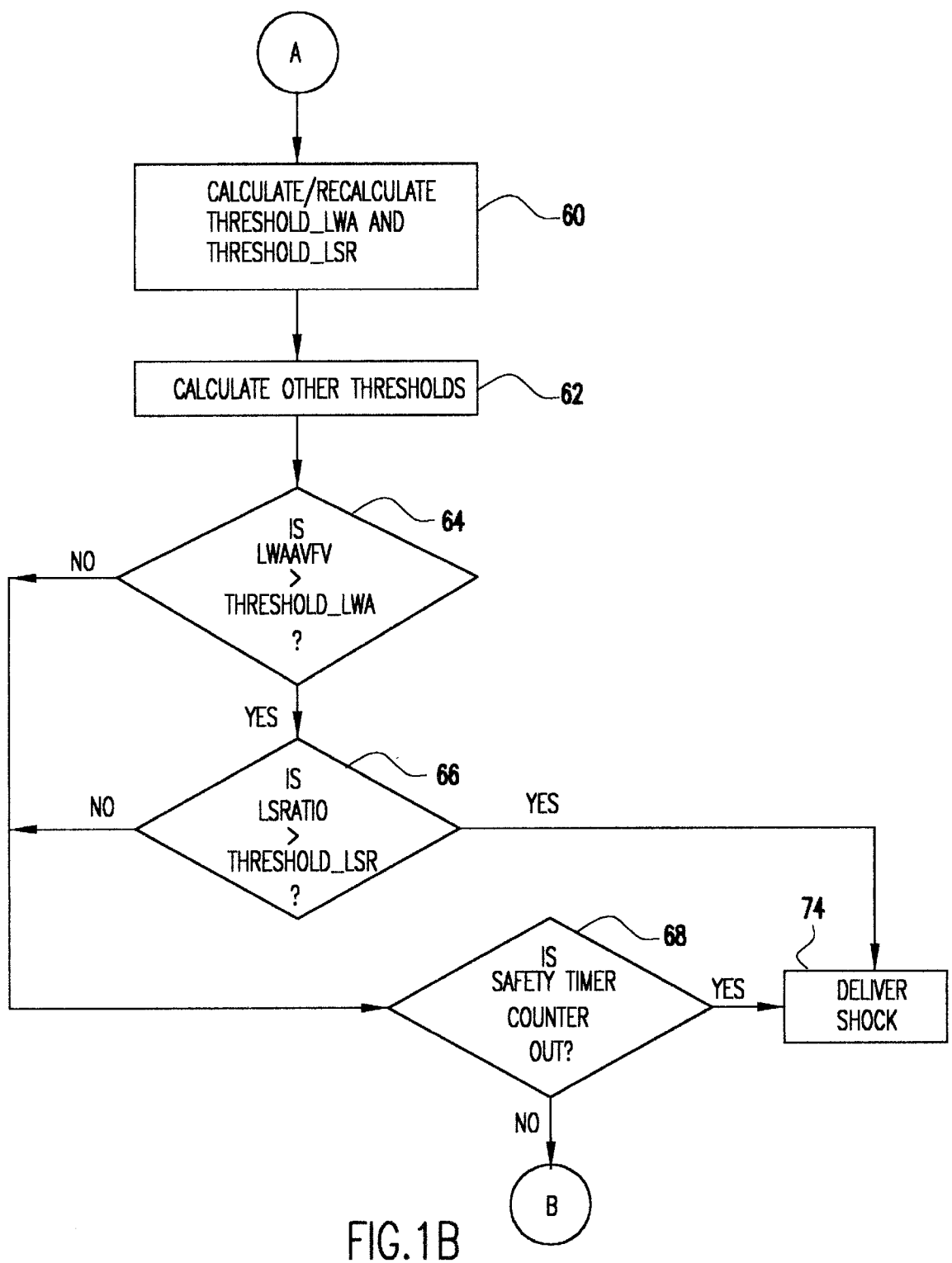

AVFVtw, LWAtw, SWAtw and LSRtw: Threshold Weight (tw) for each corresponding threshold listed above, i.e. these weighting factors are used to continuously updating the corresponding thresholds in real time. The value of these weights are ranged 0.3 –1.5 and each weight can independently set without any relationship to other weights. The general formula to relate these tw values to their corresponding parameters is based on the maximal values and can be expressed as the following mathematic formula:

THRESHOLD_NNNN=NNNNtw*Maximal MMMM values during a TP where NNNN is one of AVFV, LWA, SWA, and LSR, and where MMMM is one of AVFV, LWAAVFV, SWAAVFV, and LSRATIO Detailed Description FIGS. 1A–B depict the process steps for automatic thresholds detection. The process uses the new parameters, SWAAVFV and LSRATIO, as well as the LWAAVFV parameter which is described in U.S. Pat. No. 5,500,008. At step 40, the VF is detected and confirmed by an internal arrhythmia detection subsystem. The capacitor charging process is started and several counters/timers can be initialized at this time. The TP counter, defined as the Timeout Period, is of particular interest to this invention. The exact value for TP is not fixed and can vary according to different patients. The suggested values for TP is about 1–7 sec, i.e., 3 sec. It is also understood that many other non-specific parameters need to be initiated at step 40. At step 42, the current AVFV is available from a data acquisition subsystem which is also not part of this invention. The corresponding LWAAVFV, SWAAVFV and LSRATIO can be readily calculated using the current AVFV and previous AVFV values at this time. At step 44 these LWAAVFV, SWAAVFV and LSRATIO values will be compared with maximal LWAAVFV, SWAAVFV and LSRATIO values that were stored in the memory previously. The TP counter is counted down for one count at step 46 and if this TP counter is "out" or "reaches zero" (0), the current maximal LWAAVFV, SWAAVFV and LSRATIO values are stored in a memory subsystem at step 48. Thus, the old maximums from the old TP are replaced by these current maximums. Note that if the TP counter has not reached zero at step 46, the flow goes to step 50 and the initialization period is enforced in this step. The loop is continued at step 42 if the initialization period is not done at step 50. The VF episode should be reconfirmed at step 54. The shock delivery is aborted at step 56 if the VF is not re-confirmed.

With reference to FIG. 1B, the adaptive threshold values for the new shock criteria are discussed. The THRESHOLD_LWA and THRESHOLD_LSR are calculated at step 60. These parameters are re-calculated if one or more maximal values were found in step 48. Other thresholds are calculated at step 62. The shocking criteria using LWAAVFV and LSRATIO parameters is done at steps 64 and 66 respectively. If LSRATIO is greater than THRESHOLD LSR, shock is delivered immediately. In the current embodiment where the threshold weights are 90% of maximum, this results in the shock delivered during the upward slope of the fib waveform. If any criteria are not met, in order to rescue the patient's heart in time the safety timer is tested at step 68 and the shock is delivered at step 74 if the safety timer is expired. Thus a shock will be delivered under all circumtances during a pre-set safety time period. Otherwise, the loop is re-started at point B in FIG. 1A.

Figure 5A:
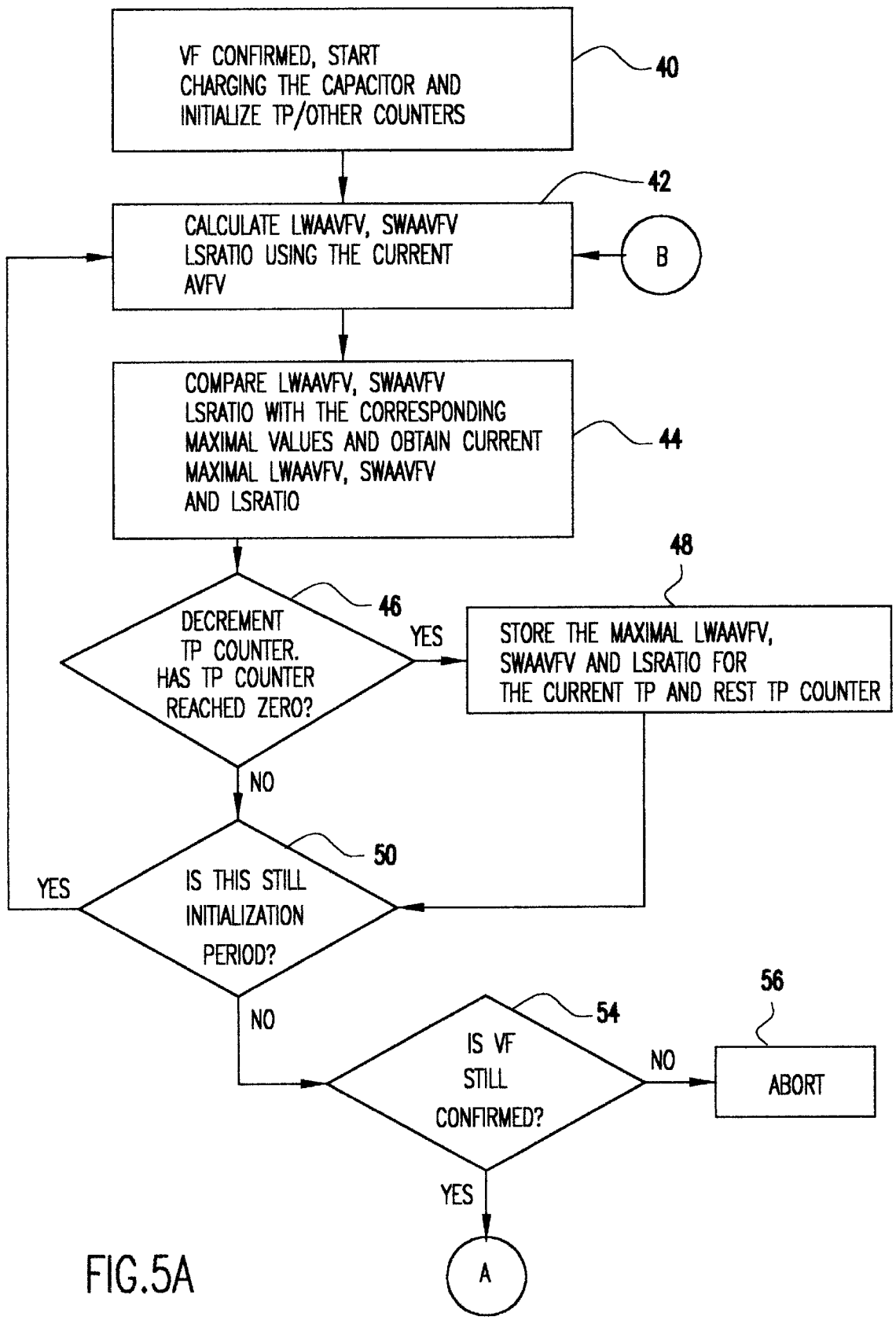
FIGS. 5A–B are flow diagrams illustrating another preferred processing of electrograms in order to deliver defibrillation energy when the heart is most susceptable to being defibrillated.
Figure 5B:
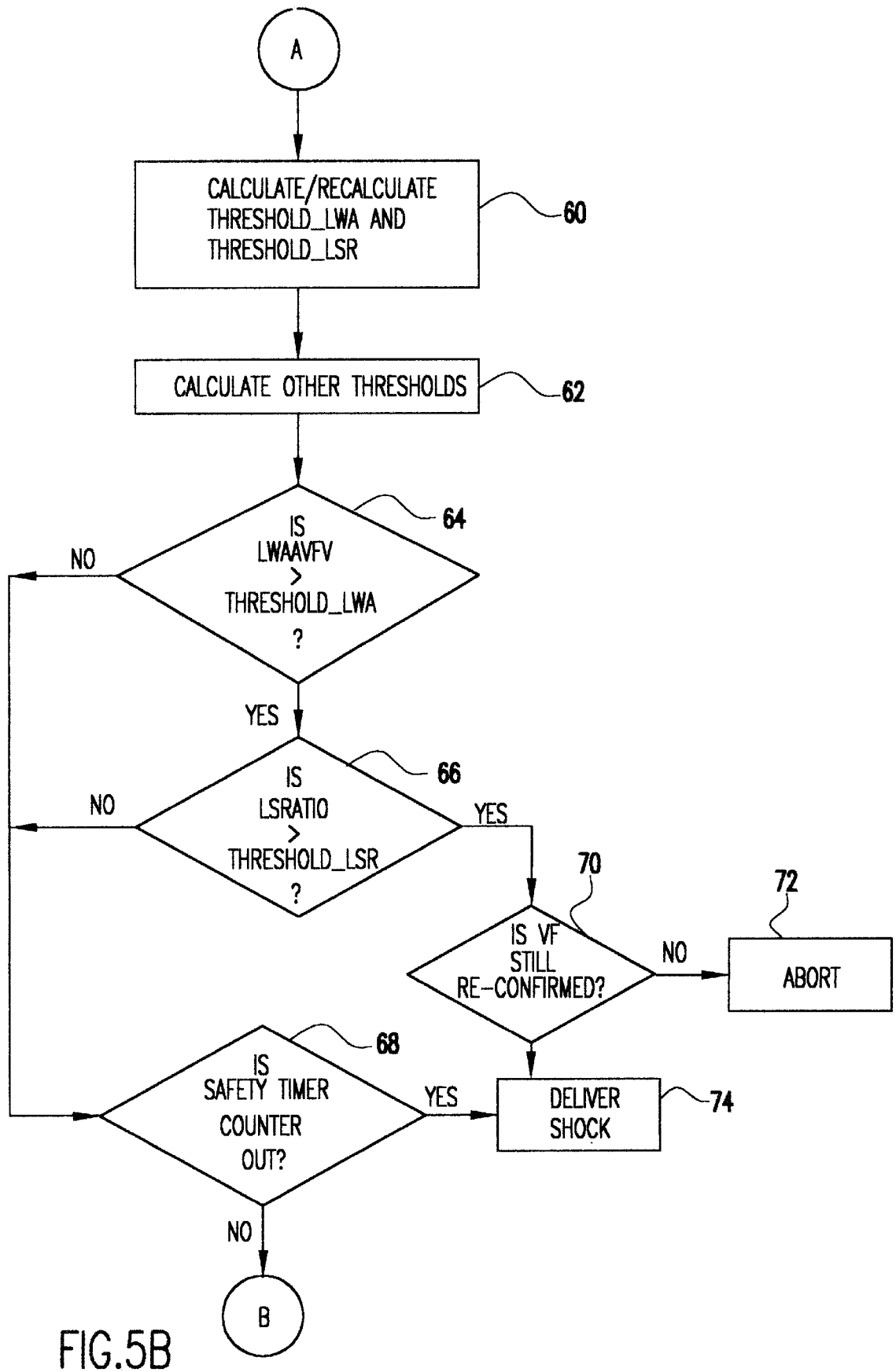

Another preferred process is illustrated in FIG. 5A–B. A step 70 for re-confirming the VF episode is implemented before delivering the shock. At steps 70 and 72, if the VF episode is not re-confirmed, the shock delivery is aborted. Otherwise, the shock is delivered immediately at step 74.

Figure 2:
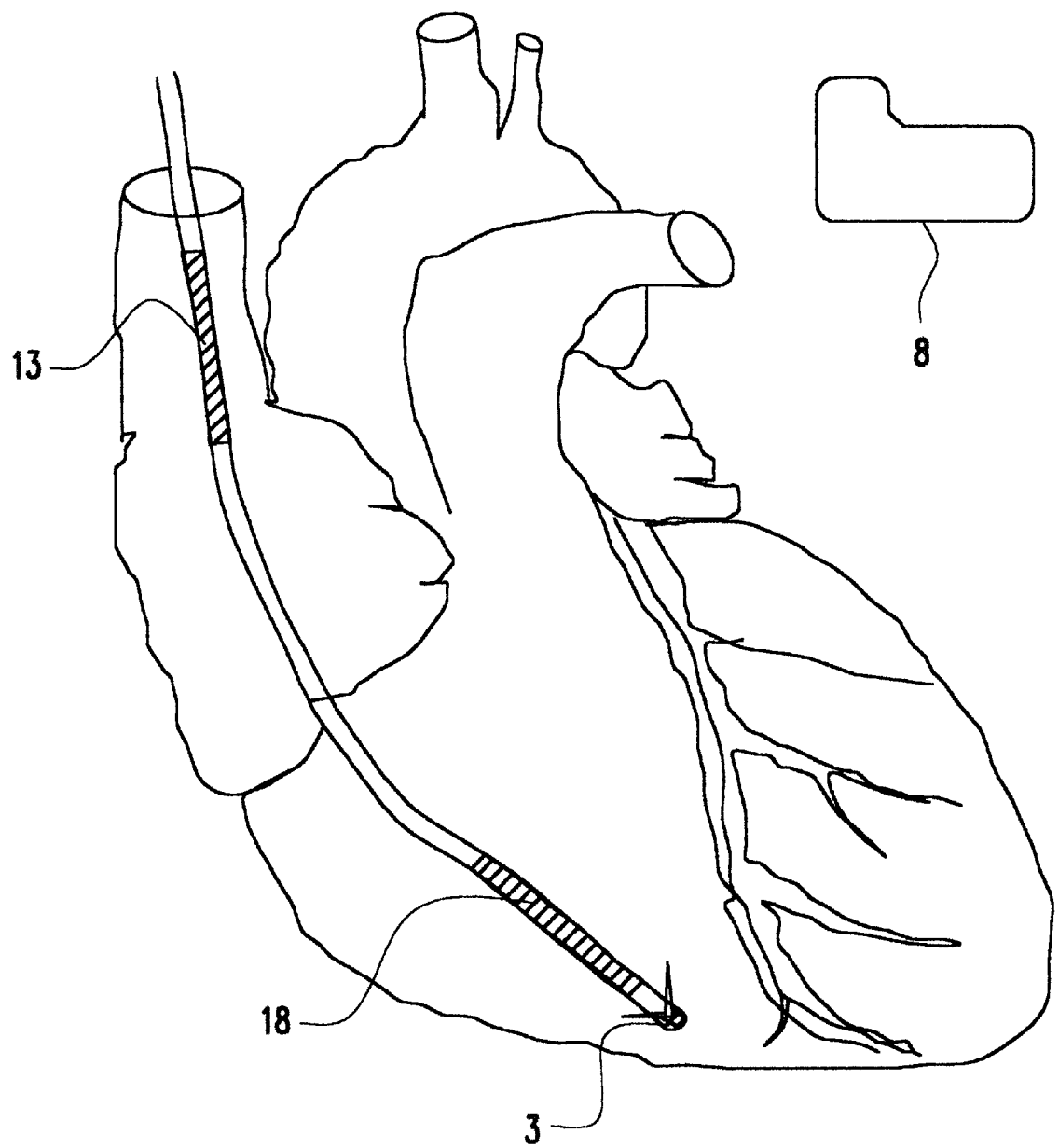
FIG. 2 is an illustration of a right ventricular (RV) pacing electrode and an electrically active pulse generator case placed subcutaneously in the patient's left pectoral region used to sense the global ventricular electrogram.

FIG. 2 is an illustration of a right ventricular (RV) pacing electrode 3 (termed tip electrode), distal coil 18 (termed RV coil), proximal coil 13 (termed Superior Vena Cava (SVC) coil) and an electrically active pulse generator can 8 which is commonly positioned subcutaneously (SubQ) in the patient's left pectoral region. The RV tip electrode 3 and generator can 8 are used to sense the global ventricular electrogram. The RV tip, RV coil and SVC coil are integrated in a single transvenous catheter. The system shown in FIG. 2 is preferred for use with this invention, however, other lead systems such as the two lead system of U.S. Pat. No. 5,500,008 can be used with this invention.

Figure 3:
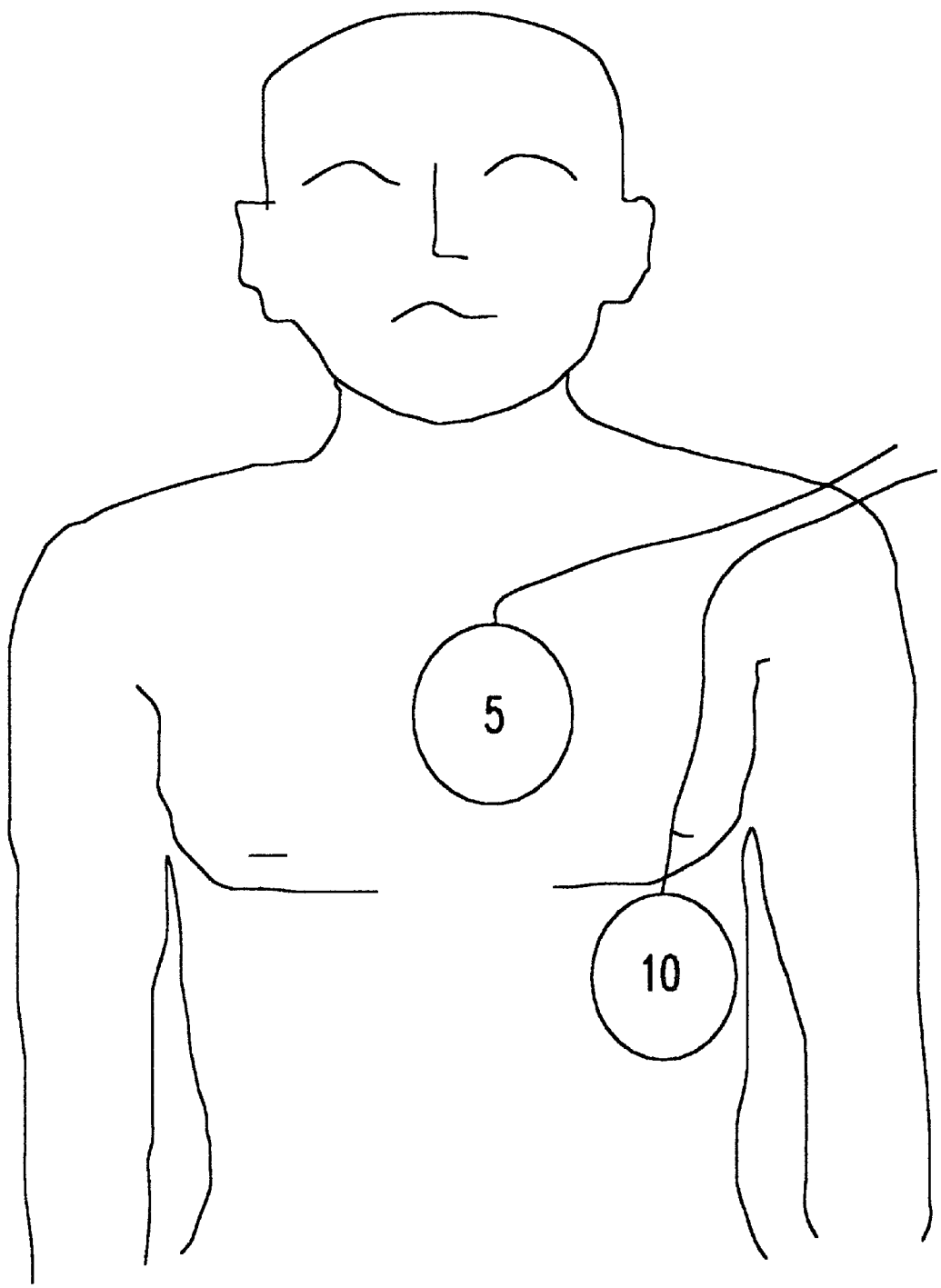
FIG. 3 is an illustration of electrode patches placed on patient's anterior torso and left lateral torso used for ventricular fibrillation waveform sensing and subsequent energy delivery during external defibrillation.
Figure 4:
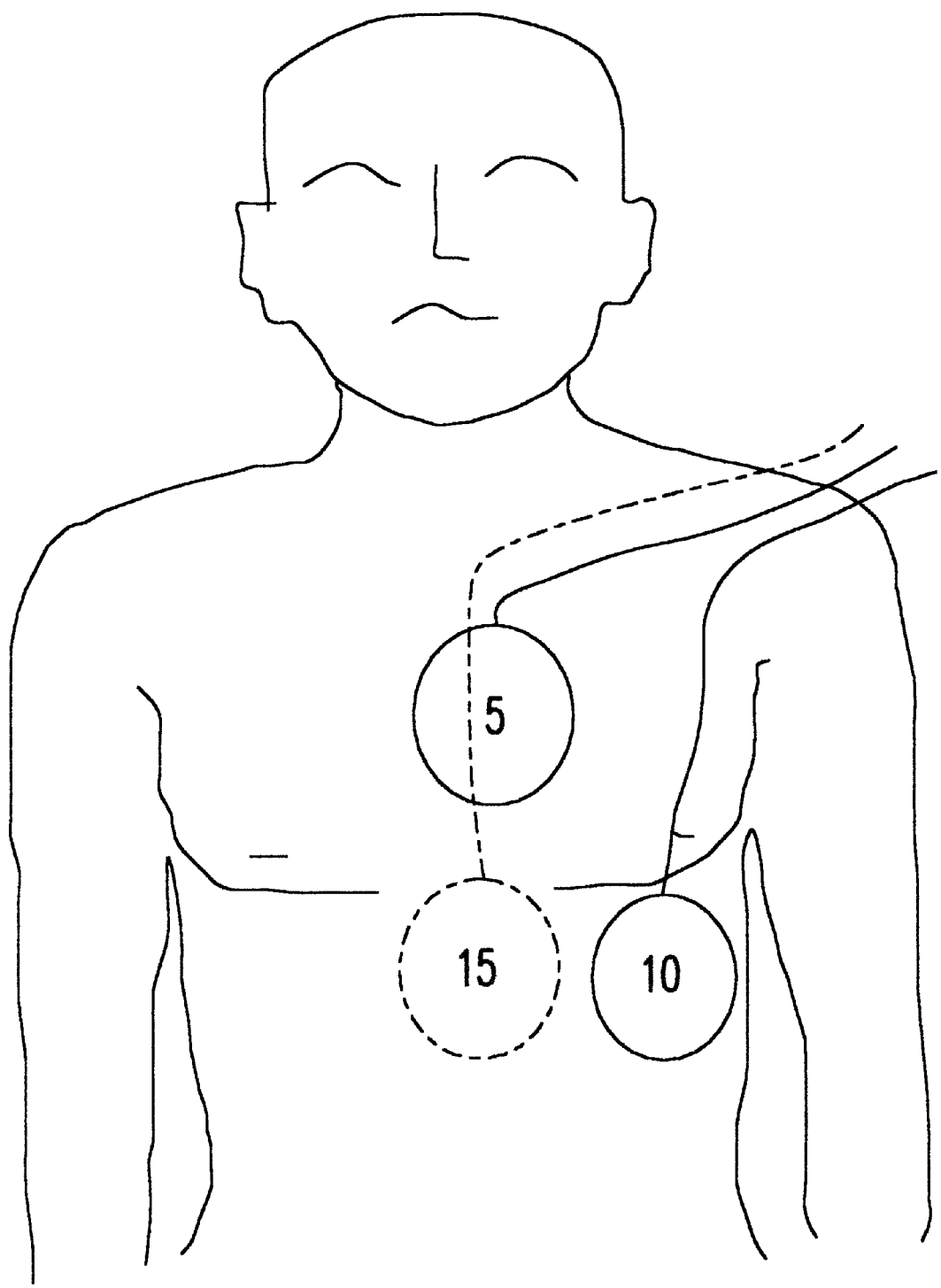
FIG. 4 is an illustration of alternate electrode placement for external defibrillation.

FIG. 3 is an illustration of one electrode patch 5 placed on a patient's anterior torso and a second electrode patch 10 on his left lateral torso. These electrode patches are commonly used for ventricular defibrillation during hospital and outside hospital ventricular fibrillation episodes. In the preferred embodiment, these two patches, 5 and 10, are used for ventricular fibrillation waveform sensing as well. In the two-electrode arrangement, the VF waveform analysis that finds an optimal time for subsequent energy delivery using electrodes 5 and 10 during external defibrillation is similar to the method described in FIGS. 1A–B. However it is also preferred to have more than one pair of electrodes during external defibrillation. FIG. 4 is an illustration of alternate electrode placement for external defibrillation in which an additional electrode 15 is placed on the patient's posterior torso. The separate VF waveform recordings can be constructed using three patch pairs, 5-10, 10-15, and 15-5. A vector waveform representing the integrated waveform from these three waveforms can be computed using the following formula:

$$V=(X^2+Y^2+Z^2)$$

where X, Y, and Z are waveforms recorded from 5-10, 10-15, and 15-5, respectively. V is the vector waveform.

While the invention has been described in terms of its preferred embodiments, those skilled in the art will recognize that the invention can be practiced with modification within the spirit and scope of the appended claims.

We claim:

1. A method for defibrillating a patient's heart with a defibrillator, comprising the steps of:

detecting and storing a fibrillation waveform recorded for the patient;

charging a high voltage capacitor in the defibrillator;

obtaining a sample of waveform parameters during said charging step, said waveform parameters including;
   (1) a maximum value of a calculated first moving rectified average, said first average based on values of said fibrillation waveform within a window of a first predetermined length of time,
   (2) a maximum value of a calculated second moving rectified average, said second average based on values of said fibrillation waveform within a window of a second predetermined length of time longer than said first predetermined length of time, and
   (3) a ratio of said first average and said second average;

determining a set of threshold values for each waveform parameter based on the sample;

continuously calculating said first and second averages and said ratio;

comparing said second average calculated in said calculating step to a first one of the threshold values;

comparing said ratio calculated in said calculating step to a second one of the threshold value; and after completion of the charging step, delivering a defibrillation shock to the patient's heart during a period of fibrillation when said second average and said ratio exceed the first and second threshold values, respectively.

2. The method of claim 1, further comprising the step of:

determining if the shock was delivered within a pre-set safety time period; and if the shock was not delivered within said safety time period, delivering a prescribed defibrillation shock at the time of expiration of said safety time period.

3. The method of claim 1 wherein the defibrillator is implantable.

4. The method of claim 1 wherein the defibrillator is external.

5. A method for defibrillating a patient's heart with a defibrillator, comprising the steps of:

detecting and storing a fibrillation waveform recorded for the patient;

charging a high voltage capacitor in the defibrillator;

obtaining a sample of waveform parameters during said charging step, said waveform parameters including;
   (1) a maximum value of a calculated first moving rectified average, said first average based on values of said fibrillation waveform within a window of a first predetermined length of time,
   (2) a maximum value of a calculated second moving rectified average, said second average based on values of said fibrillation waveform within a window of a second predetermined length of time longer than said first predetermined length of time, and
   (3) a ratio of said first average and said second average;

determining a set of adaptive threshold values for each waveform parameter based on the sample;

continuously calculating said first and second moving averages and said ratio;

comparing said second average calculated in said calculating step to a first one of the threshold values;

comparing said ratio calculated in said calculating step to a second one of the threshold values;

re-calculating said adaptive threshold values after a timeout period; and after completion of the charging step, delivering a defibrillation shock to the patient's heart during a period of fibrillation when said second average and said ratio exceed the first and second threshold values, respectively.

* * * * *